United States Patent
Raghavan et al.

(10) Patent No.: US 6,218,375 B1
(45) Date of Patent: Apr. 17, 2001

(54) COMPLEX OF RAS-FARNESYLTRANSFERASE INHIBITOR AND SULFOBUTYLETHER-7-β-CYCLODEXTRIN OR 2-HYDROXYPROPYL-β-CYCLODEXTRIN AND METHOD

(75) Inventors: Krishnaswamy S. Raghavan, Cranbury, NJ (US); Timothy M. Malloy, Bridgeport, PA (US); Sailesh A. Varia, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/483,840

(22) Filed: Jan. 17, 2000

Related U.S. Application Data
(60) Provisional application No. 60/116,647, filed on Jan. 21, 1999.

(51) Int. Cl.[7] .................................. A61K 31/715
(52) U.S. Cl. .......................... 514/58; 514/221; 514/970; 514/973; 536/103
(58) Field of Search ............. 514/58, 221, 970, 514/973; 536/103

(56) References Cited

U.S. PATENT DOCUMENTS

| | | | |
|---|---|---|---|
| 4,371,673 | 2/1983 | Pitha | 525/426 |
| 4,596,795 | 6/1986 | Pitha | 514/58 |
| 4,727,064 | 2/1988 | Pitha | 514/58 |
| 5,134,127 | 7/1992 | Stella et al. | 514/58 |
| 5,376,645 | 12/1994 | Stella et al. | 514/58 |

OTHER PUBLICATIONS

Chemical Abstracts 127:278213, "Imidazole–containing benzodiazepines and analogs as inhibitors of farnesyl protein transferase", Aug. 1997.*

Saenger, "Cyclodextrin Inclusion Compounds in Research and Industry", Angew. Chem. Int. Ed. Engl., 19, pp. 344–362 (1980).

Okimoto et al., Pharmaceutical Research, 13, pp. 256–264 (1996).

Tinwalla et al., Pharmaceutical Research, 10, pp. 1136–1143 (1993).

Szejtli, "Cyclodextrins in Drug Formulations: Part I", Pharmaceutical Technology, Jun. 1991, pp. 36–44.

Rajewski et al., Journal of Pharmaceutical Sciences, 85 (11), pp. 1142–1168 (1996).

* cited by examiner

*Primary Examiner*—Frederick Krass
(74) *Attorney, Agent, or Firm*—Timothy J. Babcock

(57) ABSTRACT

A ras-farnesyltransferase inhibitor complex formed of ras-farnesyltransferase inhibitor or a pharmaceutically acceptable salt thereof, of the formula I

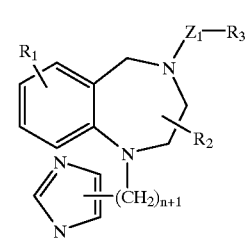

wherein n is 0 or 1; $R_1$ is selected from Cl, Br, phenyl, pyridyl or cyano; $R_2$ is aralkyl; $R_3$ is selected from lower alkyl, aryl or substituted aryl or heterocyclo; $Z_1$ is selected from CO, $SO_2$, $CO_2$, or $SO_2NR_5$, $R_5$ is selected from hydrogen, lower alkyl or substituted alkyl; and sulfobutylether-7-β-cyclodextrin or 2-hydroxypropyl-β-cyclodextrin is provided. The complex has unexpectedly high aqueous solubility of the ras-farnesyltransferase inhibitor and is useful for its intravenous delivery to humans with cancer. Also provided is a method for forming the complex. The ras-farnesyltransferase inhibitors are useful as antitumor agents.

10 Claims, No Drawings

COMPLEX OF RAS-FARNESYLTRANSFERASE INHIBITOR AND SULFOBUTYLETHER-7-β-CYCLODEXTRIN OR 2-HYDROXYPROPYL-β-CYCLODEXTRIN AND METHOD

RELATED APPLICATIONS

This application claims priority benefit under Title 35 §119(e) of U.S. Provisional Application No. 60/116,647, filed Jan. 21, 1999, and entitled COMPLEX OF RAS-FARNESYLTRANSFERASE INHIBITOR AND SULFOBUTYLETHER-7-β-CYCLODEXTRIN OR 2-HYDROXYPROPYL-β-CYCLODEXTRIN AND METHOD.

FIELD OF THE INVENTION

The present invention relates to a ras-farnesyltransferase inhibitor complex having improved water-solubility and stability, which is formed from ras-farnesyltransferase inhibitors, such as (R)-7-cyano-2,3,4,5-tetrahydro-1-(1H-imidazol-4-ylmethyl)-3-(phenylmethyl)-4-(2-thienylsulfonyl)-1H-1,4-benzodiazepine and sulfobutylether-7-β-cyclodextrin or to (R)-7-cyano-2,3,4,5-tetrahydro-1-(1H-imidazol-4-ylmethyl)-3-(phenylmethyl)-4-(2-thienylsulfonyl)-1H-1,4-benzodiazepine and 2-hydroxypropyl-β-cyclodextrin, and to methods of forming such complex. The ras-farnesyltransferase inhibitors are useful as anti-tumor agents. The complex is also useful as an anti-tumor agent.

BACKGROUND OF THE INVENTION

Cyclodextrins are cyclic oligosaccharides obtained from starch, formed of six glucose units (α-cyclodextrin), seven glucose units (β-cyclodextrin) or eight glucose units (γ-cyclodextrin). They are known to form inclusion compounds with smaller molecules which fit entirely or at least partially into the 5–8 A cyclodextrin cavity, Saenger, W., "Cyclodextrin Inclusion Compounds in Research and Industry," Angew. Chem. Int. Ed. Engl. 19, 344–362 (1980). On page 351, Saenger indicates that α-cyclodextrin forms complexes with water, methanol, polyiodide, iodine, krypton, n-propanol, p-iodoaniline, dimethyl sulfoxide and methanol, m-nitrophenol, methyl orange, prostaglandin E, potassium acetate; β-cyclodextrin forms complexes with water, n-propanol, p-iodophenol, 2,5-diiodobenzoic acid, p-nitroacetanilide; and γ-cyclodextrin forms complexes with propanol/water and water.

In addition, Saenger indicates on page 357 that β-cyclodextrin increases stabilization of benzocaine, procaine, atropine, aspirin, nitroglycerin, allicin, phenylbutazone, salicyclic acid, ascaridole, the ether ester of chaulmoogric acid, linoleic acid and indomethacin, and cyclodextrins increase water-solubility of fatty acids, amines such as procaine, lidocaine, meperdine, adipherine, steroids such as cortisone acetate and testosterone, hydroxybenzoic acid, benzocaine, aspirin, p-aminobenzoic acid, tetracycline, sulfadiazine, morphine, vanillin, ephedrine, sorbic acid, phenyl-substituted carbonic acids, ketoprofen, other antipyretic agents, vitamin $D_3$, coumarin anticoagulants, sulfonamides and barbiturates.

However, β-cyclodextrin shows nephrotoxicity and membrane destabilizing properties. Because of the safety concerns with β-cyclodextrins, numerous chemical modifications of the cyclodextrins have been made. The different types of β-cyclodextrins are alkylated cyclodextrins, hydroxyalkylated cyclodextrins, carboxymethyl cyclodextrins and the sulfoalkylether cyclodextrins which include sulfobutylether (SBE) β-cyclodextrins with degrees of substitution on 4 and 7 positions of β-cyclodextrin. The specific product in the last group includes Captisol®, an SBE 7-β-cyclodextrin (SBE-CD). The specific product in the hydroxyalkylated cyclodextrins include 2-hydroxypropyl-β-cyclodextrin (HPCD).

U.S. Pat. No. 4,371,673, issued Feb. 1, 1983, discloses two types of water soluble cyclodextrin complexes of retinoid-polymers and complexes of retinoids with ether type derivatives of cyclodextrins.

U.S. Pat. No. 4,596,795, issued Jun. 24, 1986, discloses the administration of sex hormones, particularly testosterone, progesterone and estradiol in the form of their complexes or inclusions with specific derivatives of cyclodextrins by the sublingual or buccal route resulting in effective transfer of these hormones into the systemic circulation, followed by only gradual elimination. The derivatives of cyclodextrins must carry one or several substituents, each containing one or several hydroxy group. Specially preferred are the complexes of hydroxypropylbetacyclodextrin and poly-beta-cyclodextrin.

U.S. Pat. No. 4,727,064, issued Feb. 23, 1988, is directed to the method of conversion of drug compositions which themselves are crystalline and of low water-solubility into intrinsically amorphous complexes which have improved pharmaceutical properties. This conversion is achieved by inclusion of the above drug compositions into water-soluble, multi-component mixtures of cyclodextrin derivatives. The cyclodextrin derivatives which are used are hydroxypropyl-beta-cyclodextrin, dihydroxypropyl-beta-cyclodextrin, carboxymethyl-beta-cyclodextrin, etc.

U.S. Pat. No. 5,134,127, issued Jul. 28, 1992, discloses sulfoalkyl ether cyclodextrin derivatives and their use as solubilizing agents for water insoluble drugs for oral, intranasal or parenteral administration. It also discloses a pharmaceutical composition wherein a drug is complexed to a sulfobutylether-β-cyclodextrin. The drug is selected from the group consisting of amobarbital, ampicillin, aspirin, beclomethasone, benzocaine, testosterone, etc.

U.S. Pat. No. 5,376,645, issued Dec. 27, 1994, also discloses sulfoalkylether cyclodextrin derivatives and their use as solubilizing agents for water insoluble drugs for oral, intranasal or parenteral administration. It also discloses a composition wherein a drug is complexed to a sulfobutyl ether-β-cyclodextrin. The drugs used are identical to the drugs disclosed in U.S. Pat. No. 5,134,127.

Ras-farnesyltransferase inhibitors of the formula I

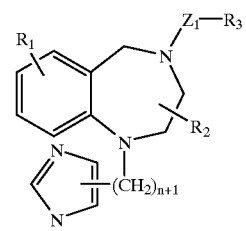

are potential anti-tumor agents having poor water-solubility and stability. Accordingly, ras-farnesyltransferase inhibitors which have improved water-solubility and stability would be a desirable addition to the anti-tumor field.

DESCRIPTION OF THE INVENTION

In accordance with the present invention, a new ras-farnesyltransferase inhibitor complex or inclusion compound is provided which is formed of ras-farnesyltransferase inhibitors of formula I or their pharmaceutically acceptable salts

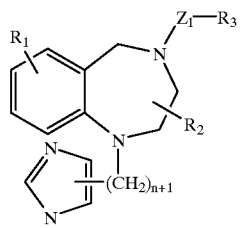

and a sulfobutylether-7-β-cyclodextrin or 2-hydroxypropyl-β-cyclodextrin. In formula I, n is 0 or 1; $R_1$ is Cl, Br, phenyl, pyridyl or cyano; $R_2$ is aralkyl; $R_3$ is lower alkyl, aryl, substituted aryl or heterocyclo; $Z_1$ is CO, $SO_2$, $CO_2$, $SO_2NR_5$ wherein $R_5$ is hydrogen, lower alkyl or substituted alkyl.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONH alkyl, CONH aryl, CONH aralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "heterocyclo" refers to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, 3, or 4 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

The inhibitors of formula I may form salts with a variety of organic and inorganic acids. Such salts include those formed with hydrogen chloride, hydroxymethane sulfonic acid, hydrogen bromide, methanesulfonic acid, sulfuric acid, acetic acid, trifluoroacetic acid, maleic acid, benzenesulfonic acid, toluenesulfonic acid and various others e.g., nitrates, phosphates, borates, tartrates, citrates, succinates, benzoates, ascorbates, salicylates and the like. Such salts may be formed by reacting inhibitor I in an equivalent amount of the acid in a medium in which the salt precipitates or in an aqueous medium followed by evaporation. The pharmaceutically and physiologically acceptable non-toxic salts are preferred, although other salts are also useful, e.g., in isolating or purifying the inhibitors of the present invention (compound 1) or its salt.

The specific inhibitors are
(R)-7-cyano-2,3,4,5-tetrahydro-1-(1H-imidazol-4-ylmethyl)-3-(phenylmethyl)-4-(2-thienylsulfonyl)-1H-1,4-benzodiazepine; (compound 1), or its salt;
(R)-2,3,4,5-tetrahydro-1-(1H-imidazol-4-ylmethyl)-4-phenylsulfonyl)-3-(phenylmethyl)-1H-1,4-benzodiazepine-7-carbonitrile, or its salt;
(R)-7-bromo-2,3,4,5-tetrahydro-1-(1H-imidazol-4-ylmethyl)-4-(methylsulfonyl)-3-(phenylmethyl)-1H-1,4-benzdiazepine, or its salt;
(R)-7-cyano-2,3,4,5-tetrahydro-1-1H-imidazol-4-ylmethyl)-3-(phenylmethyl)-4-(propylsulfonyl)-1H-1,4-benzodiazepine, or its salt; and
(R)-7-cyano-4-[(4-fluorophenyl)sulfonyl]-2,3,4,5-tetrahydro-1-(1H-imidazol-4-ylmethyl)-3-(phenylmethyl)-1H-1,4-benzodiazepine,
or its salt.

In addition, in accordance with the present invention, there is provided a new water-soluble stable form of ras-farnesyltransferase inhibitors of formula I which comprises a complex or inclusion compound of a sulfobutylether-7-β-cyclodextrin or 2-hydroxypropyl-β-cyclodextrin with ras-farnesyltransferase inhibitor of formula I. It has been found that the ras-farnesyltransferase inhibitor-sulfobutylether-7-β-cyclodextrin or 2-hydroxypropyl-β-cyclodextrin complex has a water-solubility and stability which are substantially greater than that of other ras-farnesyltransferase inhibitor formulations.

A number of other parenteral formulations of the ras-farnesyltransferase inhibitor (R)-7-cyano-2,3,4,5-tetrahydro-1-(1H-imidazol-4-ylmethyl)-3-(phenylmethyl)-4-(2-thienylsulfonyl)-1H-1,4-benzodiazepine (compound I) with cosolvents and surfactants were evaluated. The inhibitor (R)-7-cyano-2,3,4,5-tetrahydro-1-(1H-imidazol-4-ylmethyl)-3-(phenylmethyl)-4-(2-thienylsulfonyl)-1H-1,4-benzodiazepine exhibited good solubility of greater than 10 milligrams per milliliter in aqueous formulations containing a mixture of 10% ethanol and 10% Cremophor or 10% Tween 80 alone. However, these formulations have a number of disadvantages, which are: the inability to be buffered because of increased sensitivity to ions resulting in precipitation of the ras-farnesyltransferase inhibitor, the inability to be diluted which is required for intravenous administration and which causes pH variations and precipitation of the inhibitor and the toxicity of the surfactants requiring the use of premedication in the clinic. The premedication problem is often associated with the use of surfactants like Tween 80 and Cremophor.

Examples of other ras-farnesyltransferase inhibitors are
(R)-2,3,4,5-tetrahydro-1-(1H-imidazol-4-ylmethyl)-4-phenylsulfonyl)-3-(phenylmethyl)-1H-1,4-benzodiazepine-7-carbonitrile;
(R)-7-bromo-2,3,4,5-tetrahydro-1-(1H-imidazol-4-ylmethyl)-4-(methylsulfonyl)-3-(phenylmethyl)-1H-1,4-benzdiazepine;
(R)-7-cyano-2,3,4,5-tetrahydro-1-1H-imidazol-4-ylmethyl)-3-(phenylmethyl)-4-(propylsulfonyl)-1H-1,4-benzodiazepine; and
(R)-7-cyano-4-[(4-fluorophenyl)sulfonyl]-2,3,4,5-tetrahydro-1-(1H-imidazol-4-ylmethyl)-3-(phenylmethyl)-1H-1,4-benzodiazepine, or their salts.

The ras-farnesyltransferase inhibitors of formula I as well as the specific inhibitors are synthesized by methods described in WO 97/30992. The sulfobutylether-7-β-cyclodextrin (Captisol®) is obtained from Cydex Corporation, USA. 2-Hydroxypropyl-β-cyclodextrin is available from American Maize Company, U.S.A.

In general, the complex of the invention will include a molar ratio of the ras-farnesyltransferase inhibitor of the formula I to cyclodextrin of 1:2 or higher at pH values of 3 to 9.

The complex of ras-farnesyltransferase inhibitor and sulfobutylether-7-β-cyclodextrin or 2-hydroxypropyl-β-cyclodextrin may be formed by forming an aqueous solution of sulfobutylether-7-β-cyclodextrin or 2-hydroxypropyl-β-cyclodextrin and adding the freebase or various salts of the ras-farnesyltransferase inhibitor to it with stirring and adjusting the pH with an appropriate acid or well-known aqueous buffers to the desired pH value.

In a preferred method, in accordance with the present invention, the complex of the invention is formed by forming an aqueous solution of 5 grams of the sulfobutylether-7-β-cyclodextrin or 2-hydroxypropyl-β-cyclodextrin in 15 milliliters of deionized water with stirring for thirty minutes at room temperature. The pH of the solution is adjusted with hydrochloric acid to 2 or 3. To this stirred solution is added 500 milligrams of the ras-farnesyltransferase inhibitor (R)-7-cyano-2,3,4,5-tetrahydro-1-(1H-imidazol-4-ylmethyl)-3-(phenylmethyl)-4-(2-thienylsulfonyl)-1H-1,4-benzodiazepine and after the addition of the inhibitor, the solution is additionally stirred, with pH being adjusted to 4 or 4.5 with dilute hydrochloric acid or sodium hydroxide. Then the solution is filtered using a 0.22 micron filter and the filtered solution of the complex recovered.

The preferred complex of the ras-farnesyltransferase inhibitor (R)-7-cyano-2,3,4,5-tetrahydro-1-(1H-imidazol-4-ylmethyl)-3-(phenylmethyl)-4-(2-thienylsulfonyl)-1H-1,4-benzodiazepine (compound 1) and sulfobutylether-7-β-cyclodextrin or 2-hydroxypropyl-β-cyclodextrin of the invention has been found to have improved water-solubility and stability over other formulations indicated above. For example, the aqueous solubility of the inhibitor (R)-7-cyano-2,3,4,5-tetrahydro-1-(1H-imidazol-4-ylmethyl)-3-(phenylmethyl)-4-(2-thienylsulfonyl)-1H-1,4-benzodiazepine is surprisingly increased in the presence of sulfobutylether-7-β-cyclodextrin. The solubility of this inhibitor is increased from <5 µg/mL in water to 1.2 mg/mL in 5% w/v SBE-CD and ~8 mg/mL in 40% w/v SBE-CD solution at pH 8. Similarly, at pH 4.5 the solubility of this inhibitor is also increased from 0.2 mg/mL in water to ~6 mg/mL in 5% w/v SBE-CD solution and ~45 mg/mL in 40% w/v SBE-CD solution. Similarily, the solubility of the inhibitor (R)-7-cyano-2,3,4,5-tetrahydro-1-(1H-imidazol-4-ylmethyl)-3-(phenylmethyl)-4-(2-thienylsulfonyl)-1H-1,4-benzodiazepine is also substantially higher in the presence of 2-hydroxypropyl-β-cyclodextrin. The solubility of compound 1 is ~0.2 mg/ml at pH 8 and 2.7 mg/ml at pH 4.2 in 2.5% HPCD w/v solution. Thus, depending on the pH and the concentration of SBE-CD or HPCD present in solution, the aqueous solubility of this inhibitor is found to increase by 40~1600 fold.

In addition, the stability of the preferred complex is surprisingly enhanced in the presence of light. The results show that under high intensity light of about 1000 foot-candles, the rate of degradation of the ras-farnesyltransferase inhibitor (compound 1) of the complex is decreased by greater than 10 fold in a solution containing 20% w/v SBE-CD.

The enhanced aqueous solubility of the preferred complex as well as its stability in the presence of light makes it suitable for intravenous formulation, since it overcomes the disadvantage of other formulations with cosolvents and surfactants. The preferred complex of the invention overcomes ionic strength effects, which permits the use of buffers to control the pH and is fully dilutable because of a linear increase in solubility of the inhibitor as a function of SBE-CD. It also offers a choice of diluents such as electrolytes and non-electrolytes and is totally aqueous.

The complex is useful for intravenous delivery of the ras-farnesyltransferase inhibitor for the treatment of cancer in a human being.

The invention also provides a pharmaceutical formulation comprising the complex of the ras-farnesyltransferase inhibitor of formula I with the sulfobutylether-7-β-cyclodextrin or 2-hydroxypropyl-β-cyclodextrin together with a pharmaceutically acceptable carrier thereof and optionally other therapeutic and prophylactic ingredients. The carriers must be acceptable in the sense of being compatible with the other ingredients of the formula and not deleterious to recipient thereof.

The pharmaceutical formulation may be any formulation in which the complex may be administered and includes those suitable for oral, intranasal, intraoccular or parenteral including intramuscular and intravenous administration.

The carrier ingredients for the pharmaceutical formulation may include, as appropriate, diluents, buffers, flavoring agents, binders, thickeners, lubricants, preservatives and the like.

The preferred mode of administration of the complex of the present invention is parenteral, which includes subcutaneous injections, intravenous, intramuscular, intrasternal injection or infusion techniques. In addition to the treatment of warm-blooded animals such as mice, rats, dogs, cats, etc., the complex of the invention is effective in the treatment of humans with cancer.

The following Examples represent preferred embodiments of the present invention. All temperatures are expressed in degrees Centigrade unless otherwise indicated.

EXAMPLE 1

A complex formed of sulfobutylether-7-β-cyclodextrin and ras-farnesyltransferase inhibitor (R)-7-cyano-2,3,4,5-tetrahydro-1-(1H-imidazol-4-ylmethyl)-3-(phenylmethyl)-4-(2-thienylsulfonyl)-1H-1,4-benzodiazepine (compound I), in accordance with the present invention, was prepared as described below.

Five grams of sulfobutylether 7-β-cyclodextrin(SBE-CD) was weighed in a volumetric flask. To this was added with stirring at room temperature 15 mL of deionized water with frequent sonication until a clear solution was obtained. The solution was stirred for thirty (30) minutes and then was added to it with stirring a dilute hydrochloric solution until the pH of the solution was between 2 to 3. After that a 500 mg of compound I was added to the solution and the mixture stirred for additional two hours at room temperature with frequent sonication until compound I is completely dissolved. The pH of the resulting solution was adjusted between 4 and 4.5 with dilute hydrochloric acid or sodium hydroxide. After that the volume of the solution was adjusted to 25 mL with deionized water. The solution was thoroughly mixed by inverting the flask several times, and filtered through a 0.22 μm filter. The clear filtrate contained the complex of 20 mg/mL of compound I (free base equivalent) in 20% w/v SBE-CD solution.

EXAMPLE 2

Preparation of a Complex of SBE-CD and Free Base of Compound 1 in Citric Acid Buffer To a mixture of 1.6 grams of citric acid monohydrate, 0.6 grams of sodium citrate dihydrate and 40 grams of SBE-CD in a volumetric flask was added with stirring at room temperature 170 mL of deionized water. The mixture was stirred for 30 minutes with frequent sonication until a clear solution was obtained. There was added to the solution 4.0 grams of compound I. The mixture was stirred additionally for 2 hours until a clear solution was obtained. After that, the volume of the solution was adjusted to 200 mL with deionized water and the resulting solution was thoroughly mixed and filtered through a 0.22 μm filter. The clear filtrate contained the complex of 20 mg/mL of compound I (free base equivalent) in 20% w/v SBE-CD solution.

EXAMPLE 3

Preparation of a Complex of HPCD and Free Base of Compound I in Citric Acid Buffer The complex of HPCD and free base of compound 1 can be prepared by substituting in the above procedure of Example 2 HPCD for SBE-CD.

EXAMPLE 4

Preparation of a Complex of SBE-CD and Mesylate Salt of Compound I in Citric Acid Buffer To a mixture of 1.2 grams of citric acid monohydrate, 1.2 grams of sodium citrate dihydrate and 40 grams of SBE-CD was added with stirring at room temperature 170 mL of deionized water. The mixture was stirred for 30 minutes with frequent sonication until a clear solution was obtained. After that 4–8 grams of the mesylate salt of compound I was added to the solution and the mixture stirred for an additional two hours until a solution was obtained. After that the volume of the solution was adjusted to 200 mL with deionized water and the resulting solution was thoroughly mixed and filtered through 0.22 μm filter. The clear filtrate contained a complex of 20 mg/mL of compound I (free base equivalent) in 20% w/v SBE-CD solution.

What is claimed is:

1. A ras-farnesyltransferase inhibitor complex comprising the ras-farnesyltransferase inhibitor or a pharmaceutically acceptable salt thereof

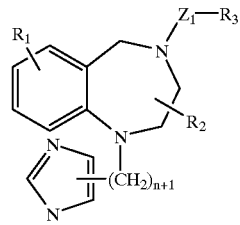

wherein n is 0 or 1; $R_1$ is Cl, Br, phenyl, pyridyl or cyano; $R_2$ is aralkyl; $R_3$ is lower alkyl, aryl, substituted aryl or heterocyclo; $Z_1$ is CO, $SO_2$, $CO_2$, or $SO_2NR_5$, $R_5$ is hydrogen, lower alkyl or substituted alkyl; and sulfobutylether-7-β-cyclodextrin or 2-hydroxypropyl-β-cyclodextrin in a molar ratio of the inhibitor to sulfobutylether-7-β-cyclodextrin or 2-hydroxypropyl-β-cyclodextrin of within the range of from about 1 to 2 or higher.

2. The complex of claim 1, wherein the inhibitor is selected from the group consisting of, (R)-7-cyano-2,3,4,5-tetrahydro-1-(1H-imidazol-4-ylmethyl)-3-(phenylmethyl)-4-(2-thienylsulfonyl)-1H-1,4-benzodiazepine;

(R)-2,3,4,5-tetrahydro-1-(1H-imidazol-4-ylmethyl)-4-phenylsulfonyl)-3-(phenylmethyl)-1H-1,4-benzodiazepine-7-carbonitrile;

(R)-7-bromo-2,3,4,5-tetrahydro-1-(1H-imidazol-4-ylmethyl)-4-(methylsulfonyl)-3-(phenylmethyl)-1H-1,4-benzdiazepine;

(R)-7-cyano-2,3,4,5-tetrahydro-1-1H-imidazol-4-ylmethyl)-3-(phenylmethyl)-4-(propylsulfonyl)-1H-1,4-benzodiazepine; and (R)-7-cyano-4-[(4-fluorophenyl)sulfonyl]-2,3,4,5-tetrahydro-1-(1H-imidazol-4-ylmethyl)-3-(phenylmethyl)-1H-1,4-benzodiazepine.

3. The complex of claim 2, wherein the inhibitor is (R)-7-cyano-2,3,4,5-tetrahydro-1-(1H-imidazol-4-ylmethyl)-3-(phenylmethyl)-4-(2-thienylsulfonyl)-1H-1,4-benzodiazepine.

4. A ras-farnesyltransferase inhibitor composition, comprising an effective amount of the complex as defined in claim 1 and a pharmaceutically acceptable carrier therefor.

5. The composition of claim 4, wherein said composition is in liquid form.

6. The composition of claim 4, wherein the carrier is citric acid buffer.

7. The composition of claim 4, which further comprises a diluent of an electrolyte or a nonelectrolyte.

8. The composition of claim 4, wherein the inhibitor is (R)-7-cyano-2,3,4,5-tetrahydro-1-(1H-imidazol-4-ylmethyl)-3-(phenylmethyl)-4-(2-thienylsulfonyl)-1H-1,4-benzodiazepine, or its pharmaceutically acceptable salt.

9. A pharmaceutical composition for parenteral administration, comprising a pharmaceutically suitable carrier and a complex of claim 1.

10. The composition of claim 9, wherein the inhibitor is (R)-7-cyano-2,3,4,5-tetrahydro-1-(1H-imidazol-4-ylmethyl)-3-(phenylmethyl)-4-(2-thienylsulfonyl)-1H-1,4-benzodiazepine, or its pharmaceutically acceptable salt.

* * * * *